US010681339B2

(12) United States Patent
Ootsuki

(10) Patent No.: US 10,681,339 B2
(45) Date of Patent: Jun. 9, 2020

(54) SURGICAL MICROSCOPE, IMAGE PROCESSING DEVICE, AND IMAGE PROCESSING METHOD

(71) Applicant: SONY CORPORATION, Tokyo (JP)

(72) Inventor: Tomoyuki Ootsuki, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 3 days.

(21) Appl. No.: 15/767,735

(22) PCT Filed: Oct. 12, 2016

(86) PCT No.: PCT/JP2016/080221
§ 371 (c)(1),
(2) Date: Apr. 12, 2018

(87) PCT Pub. No.: WO2017/073323
PCT Pub. Date: May 4, 2017

(65) Prior Publication Data
US 2018/0309980 A1 Oct. 25, 2018

(30) Foreign Application Priority Data
Oct. 26, 2015 (JP) .................................. 2015-209534

(51) Int. Cl.
H04N 13/30 (2018.01)
A61F 9/007 (2006.01)
(Continued)

(52) U.S. Cl.
CPC ............... H04N 13/30 (2018.05); A61B 3/13 (2013.01); A61B 90/20 (2016.02); A61F 9/007 (2013.01);
(Continued)

(58) Field of Classification Search
CPC ................................ A61B 90/20; H04N 13/30
See application file for complete search history.

(56) References Cited

U.S. PATENT DOCUMENTS

| 5,865,829 A * | 2/1999 | Kitajima | A61B 3/1241 359/351 |
| 2007/0070294 A1 | 3/2007 | Kim | |
| 2007/0203413 A1* | 8/2007 | Frangioni | A61B 5/415 600/478 |
| 2008/0079828 A1 | 4/2008 | Izawa | |
| 2008/0111894 A1* | 5/2008 | Tanimoto | H04N 5/33 348/222.1 |

FOREIGN PATENT DOCUMENTS

| DE | 4320579 A | 12/1993 |
| JP | 05-344997 A | 12/1993 |
| (Continued) | | |

OTHER PUBLICATIONS

International Search Report and Written Opinion of PCT Application No. PCT/JP2016/080221, dated Jan. 10, 2017, 09 pages.

Primary Examiner — Girumsew Wendmagegn
(74) Attorney, Agent, or Firm — Chip Law Group

(57) ABSTRACT

A surgical microscope is provided with a light receiving unit including at least a pixel having sensitivity to an infrared region, an imaging optical system which guides image light of an eye which is light reflected from the eye as an operation target to the light receiving unit, and a presentation unit which presents an image based on a sensor signal generated by the light receiving unit. The present technology is applicable to, for example, the surgical microscope used for an eye operation and the like.

16 Claims, 19 Drawing Sheets

(51) Int. Cl.
  *A61B 90/20* (2016.01)
  *A61B 3/13* (2006.01)
  *H04N 13/239* (2018.01)
  *G02B 21/00* (2006.01)
  *G02B 21/36* (2006.01)
  *H04N 5/33* (2006.01)
  *A61B 3/00* (2006.01)

(52) U.S. Cl.
  CPC ....... *G02B 21/0012* (2013.01); *G02B 21/361* (2013.01); *G02B 21/367* (2013.01); *G02B 21/368* (2013.01); *H04N 5/332* (2013.01); *H04N 13/239* (2018.05); *A61B 3/0008* (2013.01)

(56) References Cited

FOREIGN PATENT DOCUMENTS

| | | | |
|---|---|---|---|
| JP | 2007-534428 | A | 11/2007 |
| JP | 2008-092247 | A | 4/2008 |
| JP | 2013-162339 | | 8/2013 |
| JP | 2013-162339 | A | 8/2013 |
| JP | 5408574 | B2 | 2/2014 |
| WO | 2005/104929 | A1 | 11/2005 |
| WO | 2013/118337 | A1 | 8/2013 |

* cited by examiner

FIG. 4
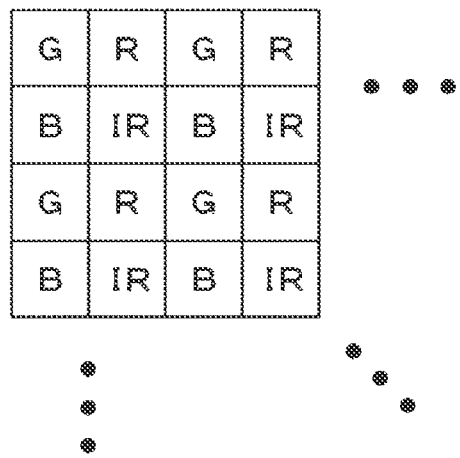
FIG. 5
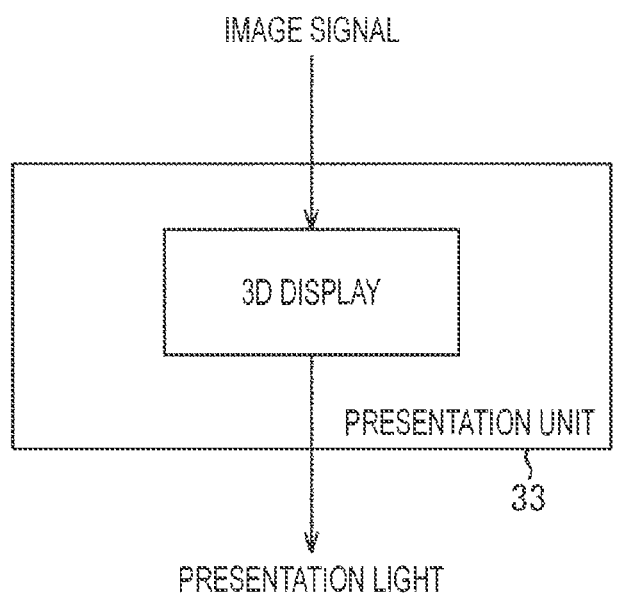
FIG. 6
| | NUMBER OF PIXELS (HORIZONTAL × VERTICAL) |
|---|---|
| RESOLUTION 1 | 1280 × 720 (HD) |
| RESOLUTION 2 | 1920 × 1080 (FULL HD) |
| RESOLUTION 3 | 3840 × 2160, 4096 × 2160 (4K) |

SURGICAL MICROSCOPE, IMAGE PROCESSING DEVICE, AND IMAGE PROCESSING METHOD

CROSS REFERENCE TO RELATED APPLICATIONS

This application is a U.S. National Phase of International Patent Application No. PCT/JP2016/080221 filed on Oct. 12, 2016, which claims priority benefit of Japanese Patent Application No. JP 2015-209534 filed in the Japan Patent Office on Oct. 26, 2015. Each of the above-referenced applications is hereby incorporated herein by reference in its entirety.

TECHNICAL FIELD

The present technology relates to a surgical microscope, an image processing device, and an image processing method, and especially relates to the surgical microscope, the image processing device, and the image processing method which facilitate observation of a site to be operated.

BACKGROUND ART

A surgical microscopic examination system for an operation on the eye such as a corneal transplantation operation and a cataract operation is developed. For example, Patent Document 1 discloses a surgical microscopic examination system provided with a microscopic examination optical system including an objective lens and an eyepiece which observes by three methods: a method of observing the eye as an operation target via an eyepiece, a method of observing the same via an image displayed on a display device, and a method of observing the same via an image displayed on a head-mounted display device.

CITATION LIST

Patent Document

Patent Document 1: Japanese Patent No. 5408574

SUMMARY OF THE INVENTION

Problems to be Solved by the Invention

However, in the conventional surgical microscope, for example, in the cataract operation on the eye with the opacified cornea, there is a case where the iris, the crystalline lens and the like inside the cornea is blurred due to opacity of the cornea, and the site to be operated is viewed with difficulty.

The present technology is achieved in view of such a situation, and an object thereof is to facilitate the observation of the site to be operated.

Solutions to Problems

A surgical microscope according to a first aspect of the present technology is provided with a light receiving unit including at least a pixel having sensitivity to an infrared region, an imaging optical system which guides image light of an eye which is light reflected from the eye as an operation target to the light receiving unit, and a presentation unit which presents an image based on a sensor signal generated by the light receiving unit.

In the first aspect of the present technology, the light receiving unit is included, the image light of the eye which is the light reflected from the eye as the operation target is guided to the light receiving unit including at least the pixel having sensitivity to the infrared region, and the image based on the sensor signal generated by the light receiving unit is presented.

An image processing device according to a second aspect of the present technology is provided with an image mixing unit which obtains an infrared light image obtained by imaging an eye as an operation target with an imaging unit having sensitivity to an infrared region and a visible light image obtained by imaging the eye with an imaging unit having sensitivity to a visible light region, and performs mixture processing on the infrared light image and the visible light image to generate a mixed image.

The image processing method according to the second aspect of the present technology includes a step of obtaining an infrared light image obtained by imaging an eye as an operation target with an imaging unit having sensitivity to an infrared region and a visible light image obtained by imaging the eye with an imaging unit having sensitivity to a visible light region, and performing mixture processing on the infrared light image and the visible light image to generate a mixed image.

In the second aspect of the present technology, an infrared light image obtained by imaging an eye as an operation target with an imaging unit having sensitivity to an infrared region and a visible light image obtained by imaging the eye with an imaging unit having sensitivity to a visible light region are obtained, and mixture processing on the infrared light image and the visible light image is performed to generate a mixed image.

The image processing device may be an independent device or may be an internal block which forms one device.

Effects of the Invention

According to the first and second aspects of the present technology, it is possible to facilitate the observation of the site to be operated.

Meanwhile, the effects are not necessarily limited to the effects herein described and may include any of the effects described in the present disclosure.

BRIEF DESCRIPTION OF DRAWINGS

FIG. 4 is a view illustrating a configuration example of the image sensor.

FIG. 5 is a block diagram illustrating a configuration of a presentation unit.

FIG. 6 is a view illustrating an example of resolution of a 3D display as the image sensor and a presentation unit.

MODE FOR CARRYING OUT THE INVENTION

A mode for carrying out the present technology (hereinafter, referred to as an embodiment) is hereinafter described. Meanwhile, the description is given in the following order.
1. First Embodiment (Configuration Example without Eyepiece)
2. Second Embodiment (Configuration Example with Eyepiece)
3. Configuration Example of Computer 1. First Embodiment <1.1 Configuration Example of Surgical System>

Figure 1:
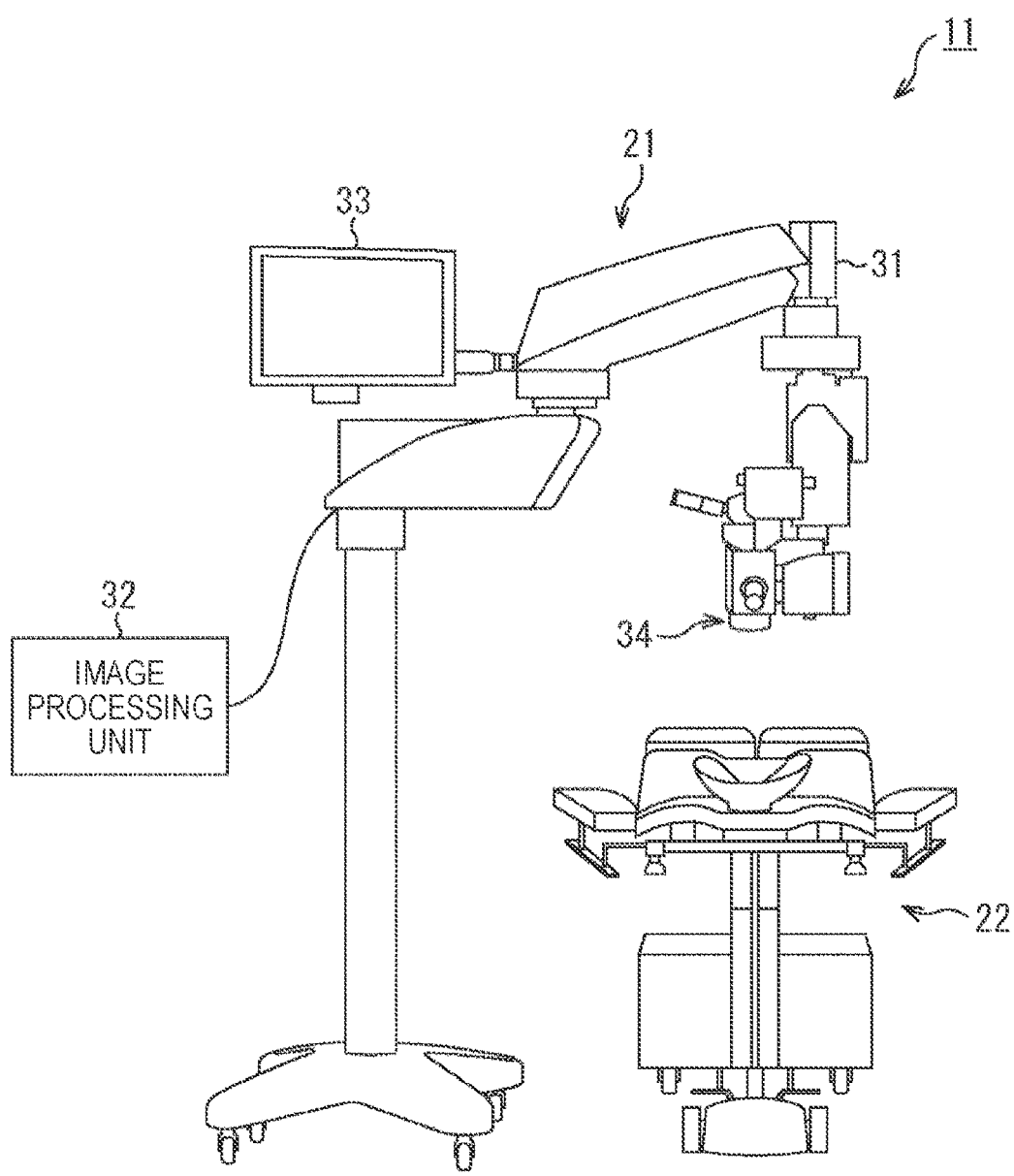
FIG. 1 is a view illustrating a configuration example of a first embodiment of a surgical system to which the present technology is applied.

FIG. 1 is a view illustrating a configuration example of a first embodiment of a surgical system to which the present technology is applied.

A surgical system 11 illustrated in FIG. 1 includes a surgical microscope 21 and a patient bed 22, and a patient undergoes an operation on the eye while lying on the patient bed 22. A doctor who is an operator performs an operation while observing the eye of the patient with the surgical microscope 21.

The surgical microscope 21 includes a casing (main body) 31, an image processing unit 32, and a presentation unit 33, and the casing 31 is provided with an objective lens 34 for magnifying observing the eye of the patient as an operation target. The image processing unit 32 includes, for example, an image processing device which performs dedicated image signal processing, a computer which operates by a predetermined program and the like. The presentation unit 33 includes, for example, a display such as an LCD and the like, and displays an image captured via the objective lens 34.

<1.2 Block Diagram of Surgical Microscope>

Figure 2:
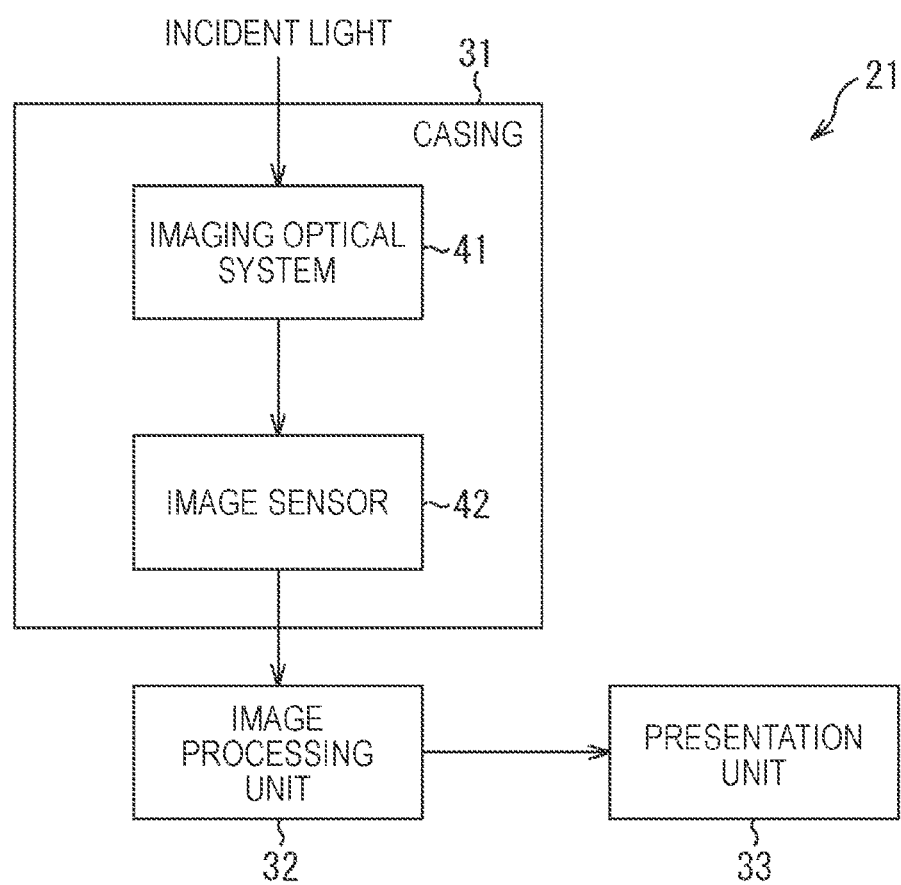
FIG. 2 is a block diagram illustrating a configuration example of a surgical microscope.

FIG. 2 is a block diagram illustrating a configuration example of the surgical microscope 21.

As described above, the surgical microscope 21 includes the casing 31, the image processing unit 32, and the presentation unit 33. The casing 31 includes an imaging optical system 41 and an image sensor 42.

The imaging optical system 41 guides light (image light of the eye) reflected from the eye of the patient as the operation target and incident thereon to the image sensor 42. The image sensor 42 being a light receiving unit that receives the image light of the eye of the patient incident via the imaging optical system 41 converts the received light into a sensor signal (electric signal) and outputs the same to the image processing unit 32.

The image processing unit 32 supplies an image based on the sensor signal supplied from the image sensor 42 to the presentation unit 33. Also, the image processing unit 32 performs predetermined image processing so that the operator may easily view an operative site on the basis of the sensor signal supplied from the image sensor 42, and supplies the image obtained as a result to the presentation unit 33. The presentation unit 33 displays the image supplied from the image processing unit 32.

<1.3 Configuration Example in Casing>

Figure 3:
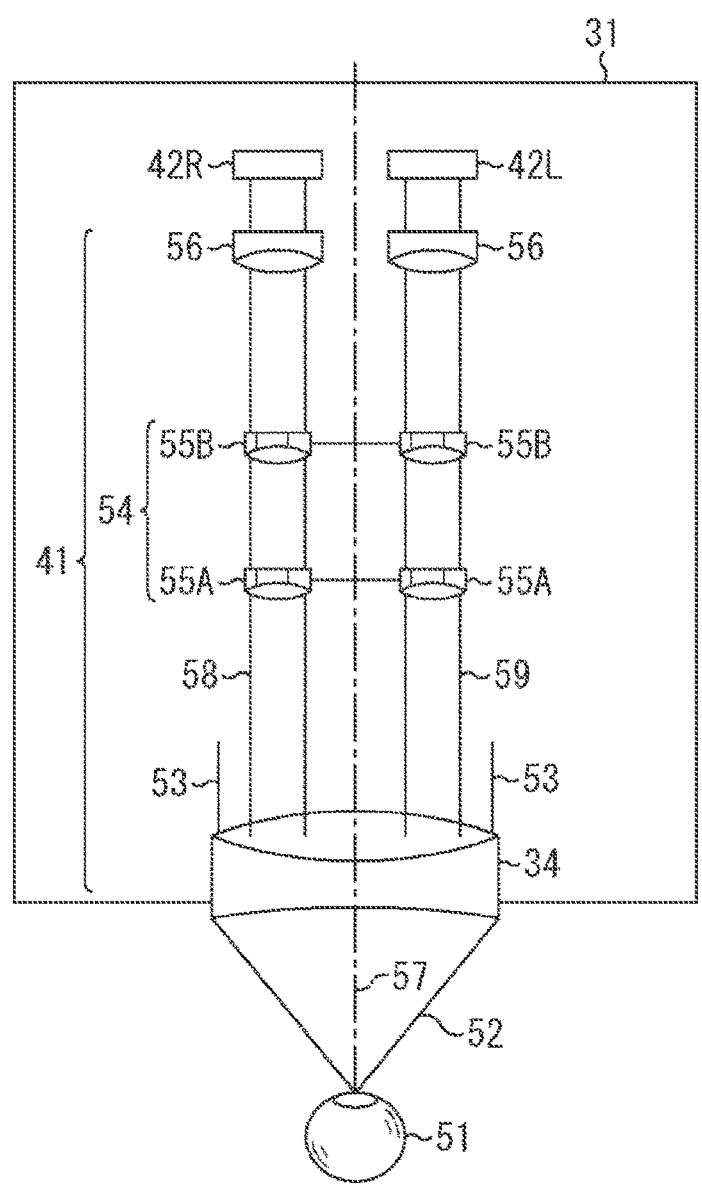
FIG. 3 is a view illustrating a more detailed configuration example of an imaging optical system and an image sensor.

FIG. 3 illustrates a more detailed configuration example of the imaging optical system 41 and the image sensor 42.

Divergent light 52 emitted from an eye 51 is converted into an image side parallel light flux 53 by the objective lens 34. The image sensor 42 includes an image sensor 42L for the left eye and an image sensor 42R for the right eye. A pair of zoom systems 54 is provided with lens groups 55A and 55B which each system may shift in a direction along an optical axis 57 of the objective lens 34 and allows two partial light fluxes 58 and 59 derived from the image side parallel light flux 53 to be incident on the image sensors 42R and 42L via a condenser lens 56, respectively.

Each of the image sensors 42L and 42R includes, for example, an imaging element such as a CMOS sensor and a CCD, and each pixel is provided with a filter which transmits light of a wavelength of any one of red (R), green (G), blue (B), and infrared (IR) as illustrated in FIG. 4. Therefore, each of the image sensors 42L and 42R is an imaging element including the pixels having sensitivity to wavelength regions of red (R), green (G), and blue (B) and the pixel having sensitivity to an IR region.

<1.4 Configuration Example of Presentation Unit>

FIG. 5 is a block diagram illustrating a configuration of the presentation unit 33.

The presentation unit 33 includes a 3D display which displays a stereoscopically viewable stereoscopic image. In other words, the presentation unit 33 is a display device which displays a right eye image and a left eye image corresponding to the light received by the image sensor 42L for the left eye and the image sensor 42R for the right eye, respectively, so that the operator who views the displayed image may perceive a stereoscopic effect (sense of depth). Examples of 3D display methods include a method using polarized glasses or shutter glasses, a method of providing lenticular lenses or a parallax barrier on a flat panel display without using the eyeglasses and the like, but the method is not limited. Also, the 3D display is not limited to a stationary display and may be a 3D head-mounted display of the type to be worn on the head of the operator, and the like.

<1.5 Example of Resolution>

FIG. 6 illustrates an example of resolution of the 3D display as the image sensors 42L and 42R and the presentation unit 33.

As the resolution of the 3D display as the image sensors 42L and 42R and the presentation unit 33, high resolution such as HD of 1280×720 pixels, full HD of 1920×1080 pixels, and 4K of 3840 (4096)×2160 pixels (horizontally× vertically) as illustrated in FIG. 6 is used, for example.

In the surgical system 11, the surgical microscope 21 converts the image light of the eye captured by the imaging optical system 41 into the sensor signal and allows the presentation unit 33 to display the same as an image. Since the operator performs an operation while viewing the image displayed on the presentation unit 33, the image displayed on the presentation unit 33 requires resolving power equal to or higher than that of an optical microscope. Therefore, when the image sensor 42 and the presentation unit 33 (3D display) have the high resolution, the operator may perform an operation while viewing only the image displayed on the presentation unit 33.

<1.6 Configuration Example of Image Processing Unit>

Figure 7:
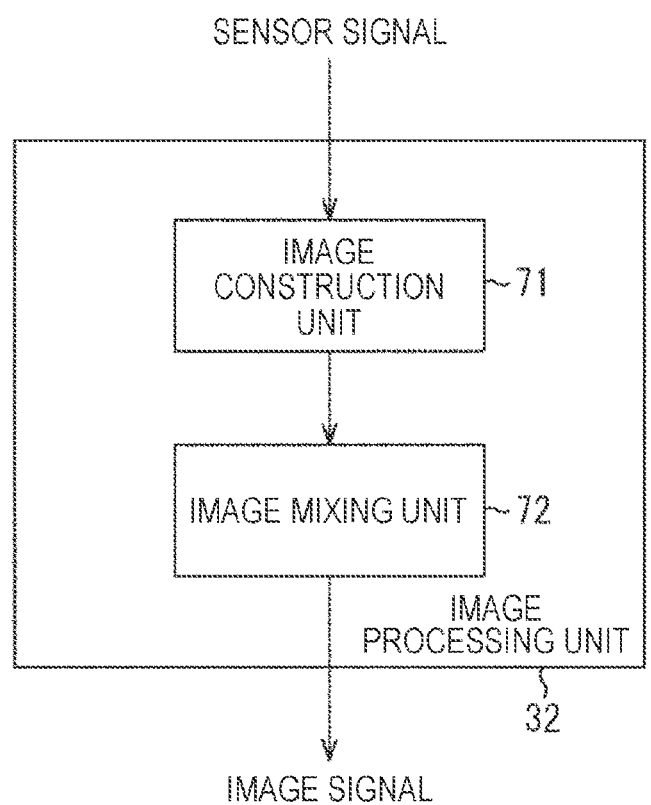
FIG. 7 is a block diagram illustrating a detailed configuration of the image processing unit.

FIG. 7 is a block diagram illustrating a detailed configuration of the image processing unit 32.

The image processing unit 32 includes an image construction unit 71 and an image mixing unit 72.

The image construction unit 71 generates a visible light image and an infrared light image using the sensor signal supplied from the image sensor 42. More specifically, the image construction unit 71 performs demosaic processing using pixel signals of R, G, B pixels, thereby generating the visible light image having any one of the resolutions illustrated in FIG. 6. Also, the image construction unit 71 generates the infrared light image by performing interpolation processing of interpolating to obtain the same resolution as that of the visible light image by using a pixel signal of an IR pixel.

The image mixing unit 72 mixes the visible light image and the infrared light image generated by the image construction unit 71 to generate a mixed image in which the operative site is more easily viewed in a cataract operation on the eye with the opacified cornea, for example, and supplies an image signal thereof to the presentation unit 33.

<1.7 Description of Processing Performed by Image Processing Unit>

Processing performed by the image processing unit 32 is described with reference to FIG. 8 to FIG. 11.

Figure 8:
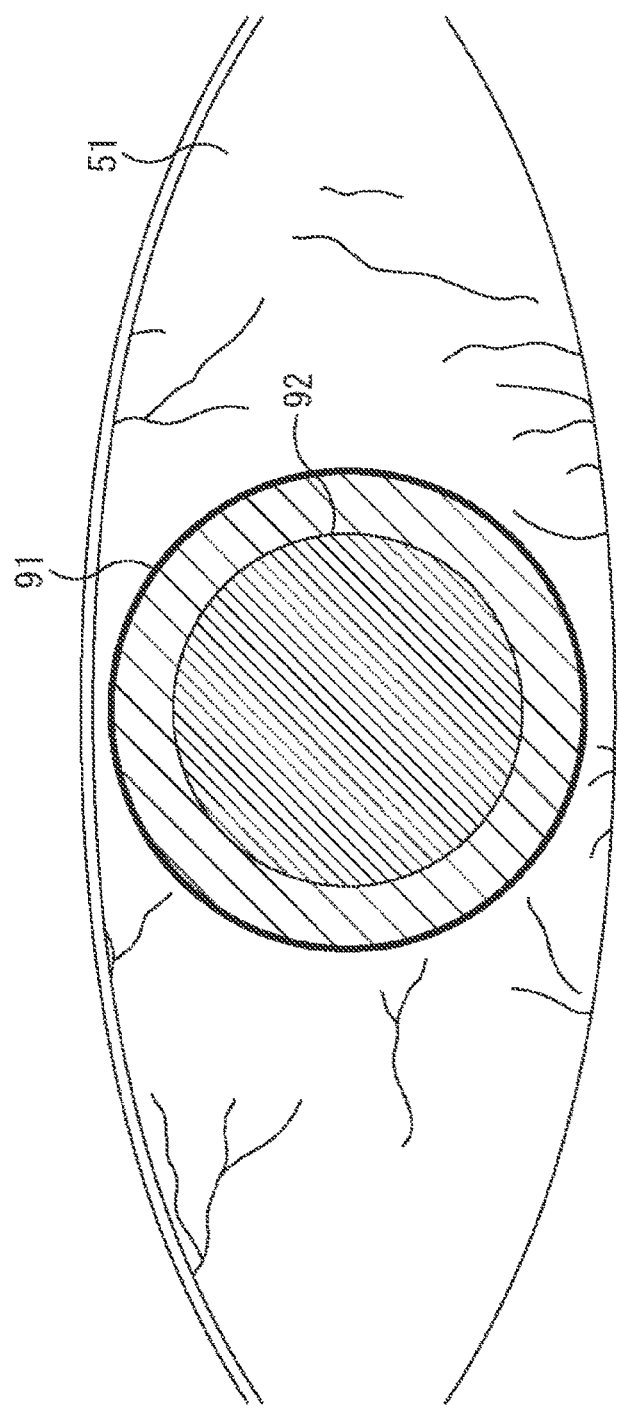
FIG. 8 is an image diagram of the eye as seen from the front.

FIG. 8 is an image diagram of the eye 51 as seen from the front.

In a case where the eye 51 is caught by the image sensor 42 from the front, the cornea 91 and the pupil 92 inside the cornea 91 may be recognized. Regions of the cornea 91 and the pupil 92 may be identified by, for example, image processing (image recognition).

Figure 9:
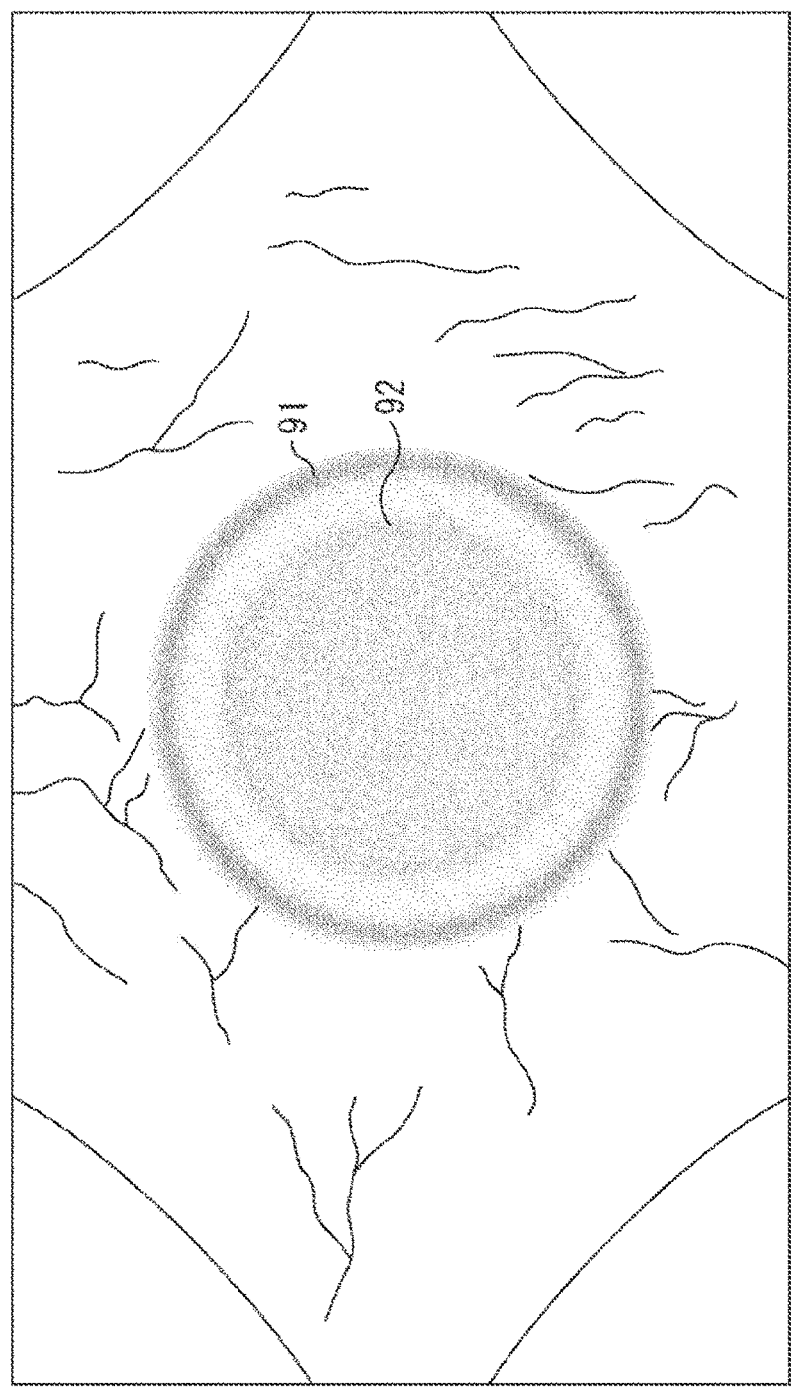
FIG. 9 is an image diagram of a visible light image during operation.

FIG. 9 is an image diagram of the visible light image during an operation generated on the basis of the pixel signals of the R, G, and B pixels of the image sensor 42 in the cataract operation on the eye with the opacified cornea.

In the cataract operation on the eye with the opacified cornea, the cornea 91 is blurred in the visible light image due to opacity of the cornea 91. FIG. 9 illustrates a monochrome image (black-to-white image) due to limitations of the drawing, but an actual visible light image is a color image.

Figure 10:
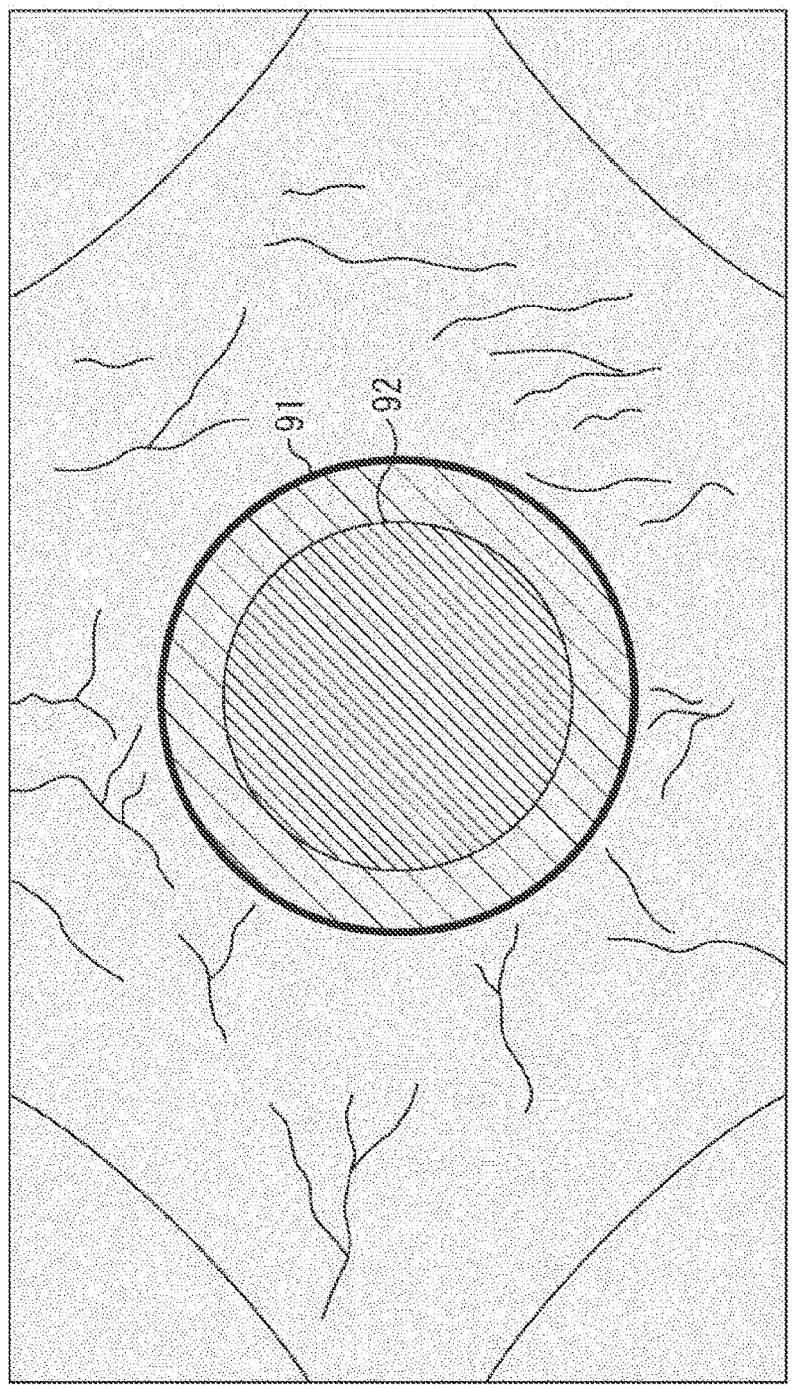
FIG. 10 is an image diagram of an infrared light image during the operation.

FIG. 10 is an image diagram of the infrared light image during an operation generated on the basis of the pixel signal of the IR pixel of the image sensor 42 in the cataract operation on the eye with the opacified cornea. In FIG. 10, a gray color in an entire image indicates that the infrared light image is the monochrome image.

In the infrared light image being the monochrome image unlike the visible light image, the region of the opacified cornea 91 is less affected by scattering due to opacity as compared with the visible light image, so that this is an image with higher contrast and with less blurring.

Figure 11:
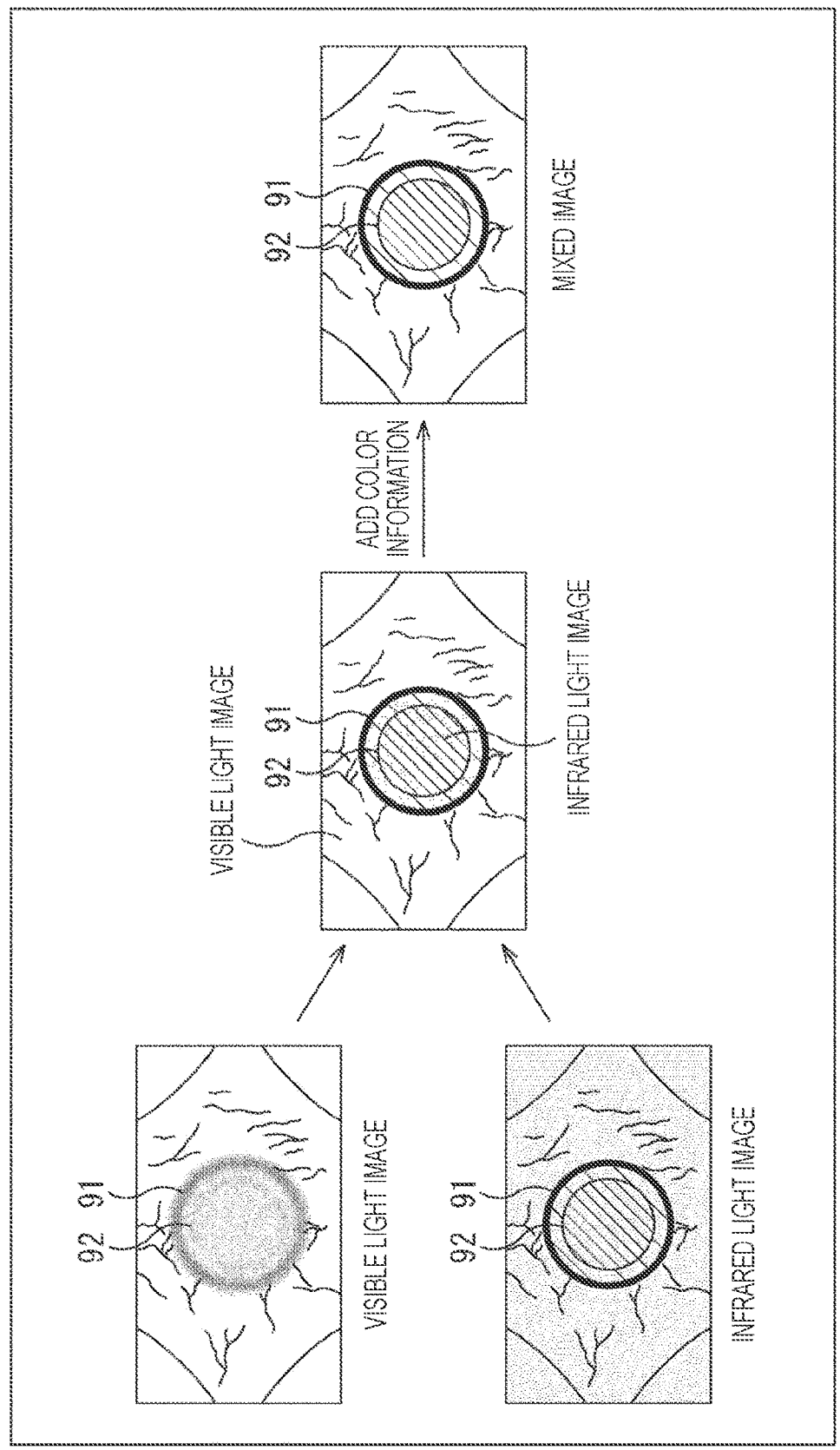
FIG. 11 is a view illustrating generation of a mixed image.

FIG. 11 is a view illustrating generation of the mixed image by the image mixing unit 72.

As for a region outside the cornea 91 of the mixed image, there is no effect of the opacity, so that the pixel value of the visible light image is used. On the other hand, as for the region of the cornea 91 of the mixed image, the pixel value of the infrared light image with high contrast less affected by the opacity is used. However, since the monochrome image is obtained by the pixel value of the infrared light image as is, the image mixing unit 72 further adds color information to the pixel value of the region of the cornea 91 adopting the pixel value of the infrared light image on the basis of chrominance information of the visible light image. As a result, the mixed image obtained by mixing the visible light image and the infrared light image is realized.

As illustrated in FIG. 11, the mixed image generated in this manner is the image with improved contrast in the region of the cornea 91 having a color familiar to the operator. Therefore, the operative site is easily viewed by the operator.

<1.8 Processing Flow of Operative Site Image Presentation Processing>

Figure 12:
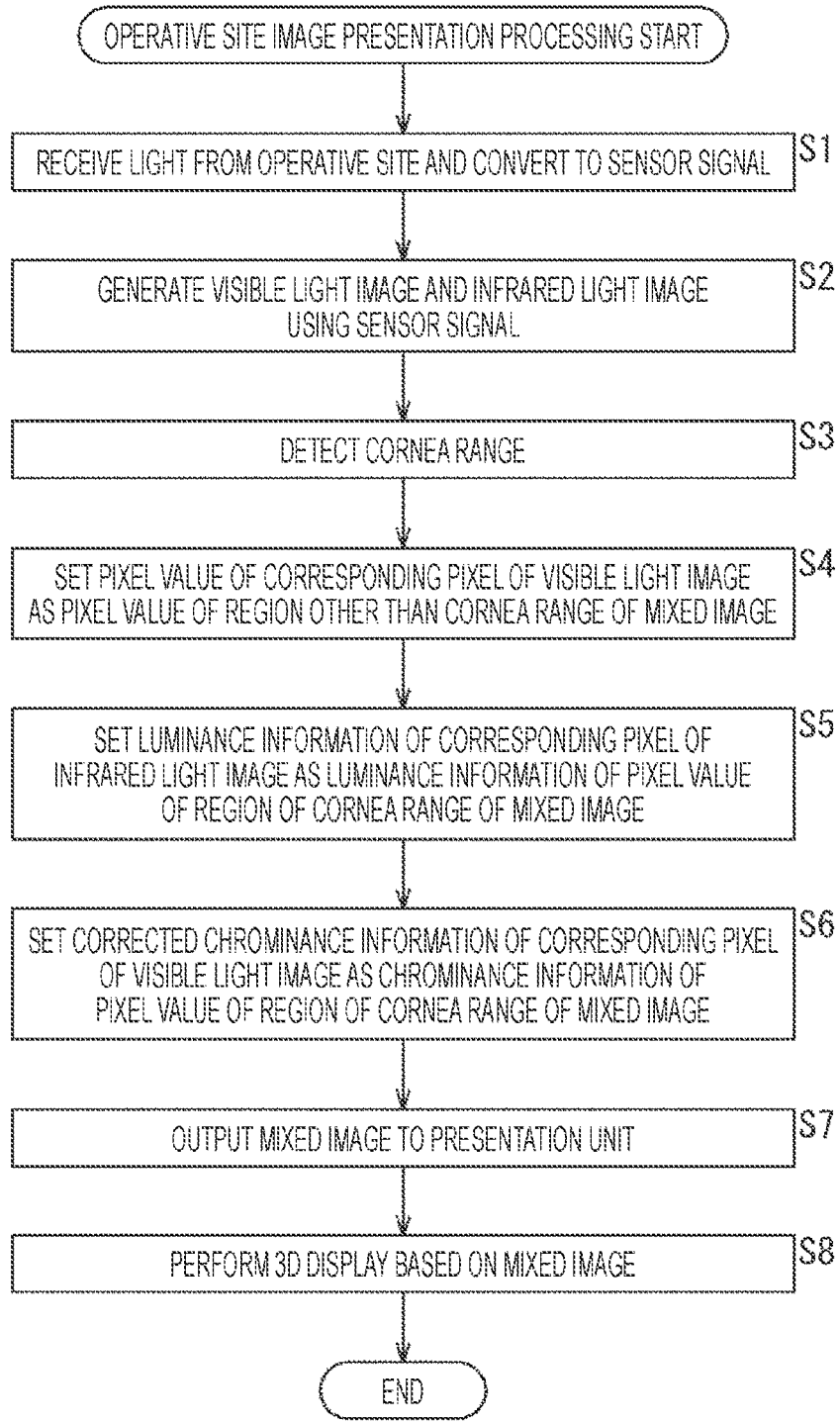
FIG. 12 is a flowchart illustrating surgical site image presentation processing.

Operative site image presentation processing of presenting an image of the operative site by the surgical microscope 21 is described with reference to a flowchart of FIG. 12.

First, at step S1, each of the image sensors 42L and 42R receives the light from the operative site (the eye of the patient) incident via the imaging optical system 41, converts the same into the sensor signal, and outputs the same to the image processing unit 32.

At step S2, the image construction unit 71 generates the visible light image and the infrared light image using the sensor signal supplied from the image sensor 42. More specifically, the image construction unit 71 generates the visible light image by performing the demosaic processing using the pixel signals of the R, G, and B pixels. Also, the image construction unit 71 generates the infrared light image by performing the interpolation processing using the pixel signal of the IR pixel. The generated visible light image and infrared light image are supplied to the image mixing unit 72. The visible light image and the infrared light image are high-resolution images having any of the resolutions illustrated in FIG. 6.

At step S3, the image mixing unit 72 detects a range of the cornea 91 (hereinafter also referred to as a cornea range) from the visible light image supplied from the image construction unit 71. Meanwhile, the cornea range may also be detected from not the visible light image but the infrared light image.

At step S4, the image mixing unit 72 sets the pixel value of a corresponding pixel of the visible light image as the pixel value of a region other than the cornea range of the mixed image to be generated. This pixel value includes luminance information and chrominance information, and at step S4, the luminance information and the chrominance information of the corresponding pixel of the visible light image are adopted as the luminance information and the chrominance information of the region other than the cornea range of the mixed image. Herein, the corresponding pixel of the visible light image is intended to mean the pixel in a position of the visible light image corresponding to the position of the pixel to which attention is paid in a case where attention is paid to each pixel forming the mixed image. The same applies to the corresponding pixel of the infrared light image.

At step S5, the image mixing unit 72 sets the luminance information of the corresponding pixel of the infrared light image as the luminance information of the pixel value of the region of the cornea range of the mixed image.

At step S6, the image mixing unit 72 sets corrected chrominance information obtained by correcting the chrominance information of the corresponding pixel of the visible light image as the chrominance information of the pixel value of the region of the cornea range of the mixed image. Herein, the corrected chrominance information is the chrominance information obtained by performing level-correction on the chrominance information of the corresponding pixel of the visible light image according to a luminance level of the infrared light image; specifically, for example, this is calculated as corrected chrominance information=(chrominance information of visible light image×(luminance information of infrared light image/luminance information of visible light image)).

At step S7, the image mixing unit 72 outputs the mixed image generated by processes at steps S4 to S6 to the presentation unit 33. The mixed image output to the presentation unit 33 becomes two types of mixed images for the right eye and the left eye corresponding to the two types of sensor signals for the right eye and the left eye generated by the image sensors 42R and 42L, respectively.

At step S8, the presentation unit 33 performs 3D display based on the mixed image for the right eye and that for the left eye supplied from the image mixing unit 72.

According to the operative site image presentation processing described above, as illustrated in FIG. 11, the mixed image displayed on the presentation unit 33 uses the pixel value of the visible light image for the region other than the cornea 91, and uses the pixel value including the luminance information of the infrared light image and the chrominance information based on the visible light image for the region of the cornea 91. As a result, it is possible to present the image with improved contrast and a color familiar to the operator for the region of the cornea 91. Especially, in a case where the contrast becomes low in the visible light image due to the eye with the opacified cornea, it is possible to present the image in which the operative site is easily viewed.

Also, since the presentation unit 33 presents the mixed image with high resolution and in 3D display, even in the operation while viewing the display, it is possible to view the operative site with similar resolving power and stereoscopic effect as in a case of viewing the operative site with the naked eye with the optical microscope.

<1.9 Variation>

Hereinafter, various variations of the above-described first embodiment are described.

<Variation of Image Sensor>

In the first embodiment described above, each of the image sensors 42L and 42R is a single plate imaging element in which each pixel which receives the light of the wavelength of R, G, B, or IR is repeatedly arranged as illustrated in FIG. 4.

Figure 13:
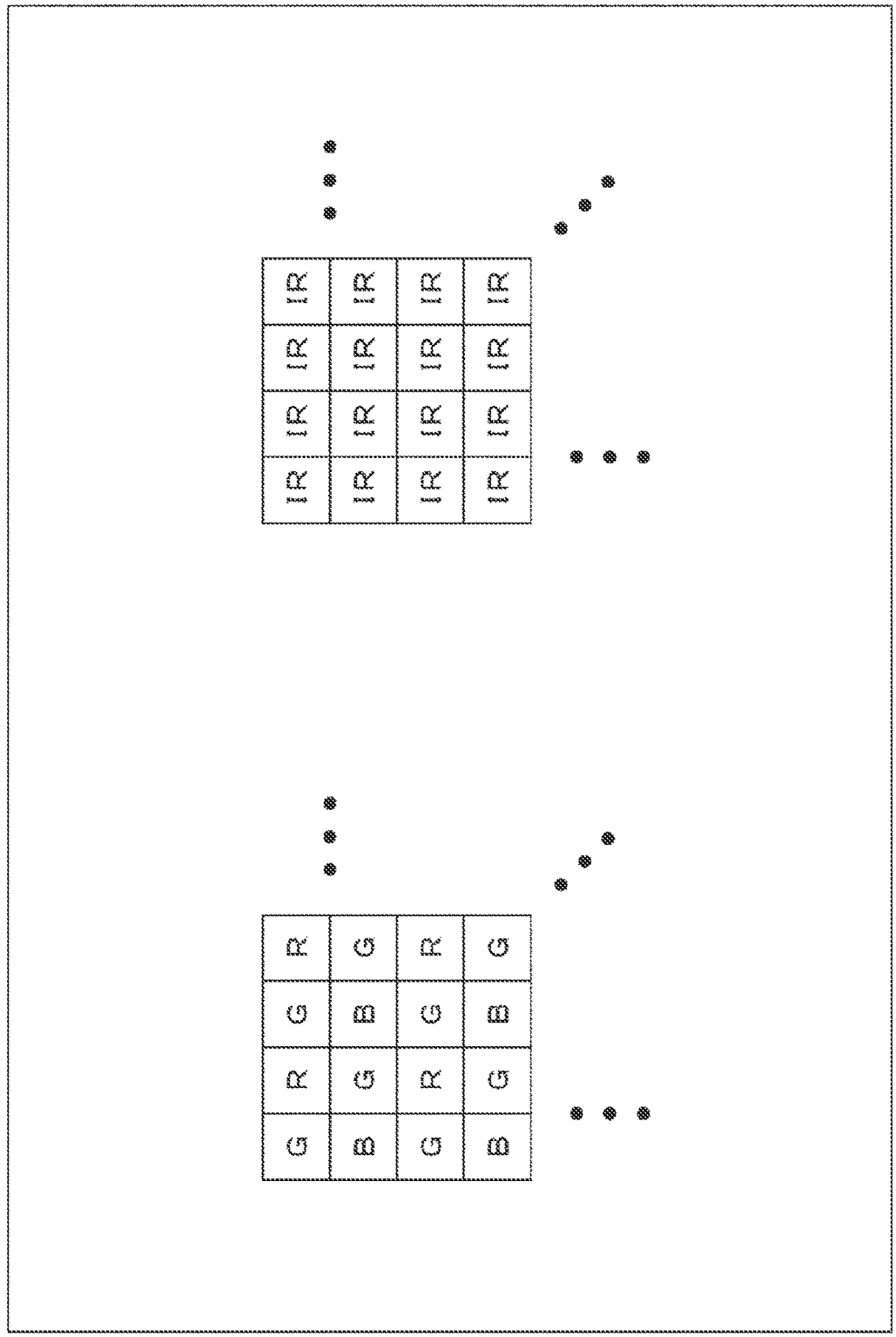
FIG. 13 is a view illustrating another example of the image sensor.

However, as illustrated in FIG. 13, each of the image sensors 42L and 42R may include a single plate imaging element in which the pixels each of which receives the light of the wavelength of R, G, or B are arranged in predetermined array such as Bayer array, and a single plate imaging element in which the pixels which receive the light of the wavelength of IR are repeatedly arranged in the horizontal and vertical directions. In this case, each of the two partial light fluxes 58 and 59 in FIG. 3 is distributed to light to the RGB imaging element and light to the IR imaging element by a half mirror or the like and is supplied to each of them.

Figure 14:
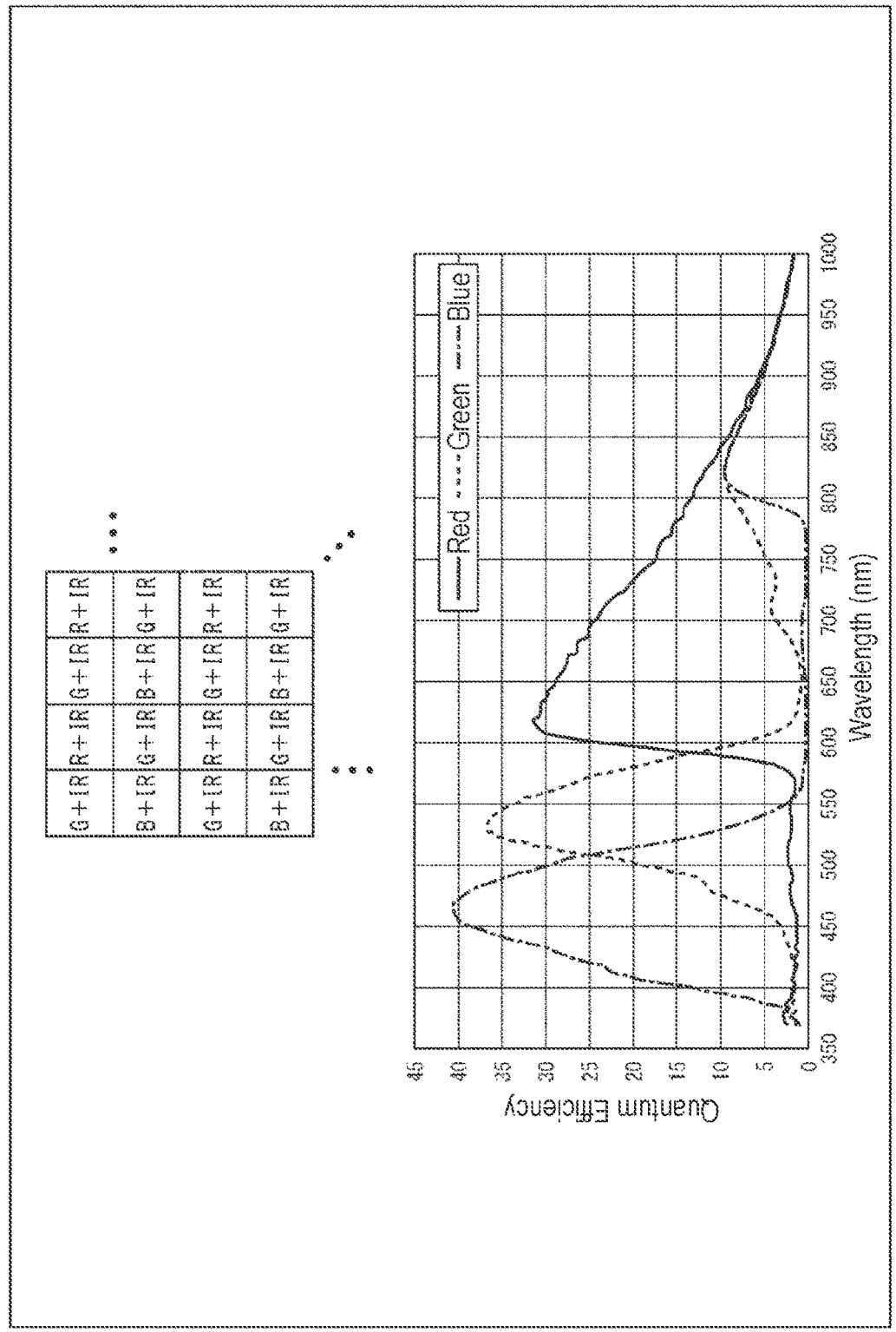
FIG. 14 is a view illustrating still another example of the image sensor.

Alternatively, each of the image sensors 42L and 42R may include a single plate imaging element in which pixels each of which receives light of a wavelength of R+IR, G+IR, or B+IR are arranged in an array similar to the Bayer array, for example, as illustrated in FIG. 14.

Herein, an R+IR pixel is the pixel having sensitivity to the wavelength region of red and infrared light, a G+IR pixel is the pixel having sensitivity to the wavelength region of green and infrared light, and a B+IR pixel is the pixel having sensitivity to the wavelength region of blue and infrared light as illustrated in received light sensitivity characteristic distribution of FIG. 14. The wavelength region of the infrared light is, for example, a region of a wavelength of 780 nm or longer.

In a case where the image sensor illustrated in FIG. 14 is adopted as the image sensors 42L and 42R, the visible light (for example, light of a wavelength of 780 nm or shorter) and the infrared light (for example, light of a wavelength longer than 780 nm) are switched in a time division manner to be applied to the operative site. Then, each of the image sensors 42L and 42R outputs the sensor signal at a timing at which the visible light is applied and the sensor signal at a timing at which the infrared light is applied in a time division manner. In the image construction unit 71, the visible light image is generated from the sensor signal at the timing at which the visible light is applied, and the infrared light image is generated from the sensor signal at the timing at which the infrared light is applied.

Configurations of the image sensors 42L and 42R are not limited to those described above, and other configurations may also be adopted.

<Variation of Mixture Processing of Visible Light Image and Infrared Light Image>

Next, a variation of the mixture processing of the visible light image and the infrared light image when generating the mixed image is described.

At step S6 of the operative site image presentation processing described above, the chrominance information obtained by performing the level-correction on the chrominance information of the corresponding pixel of the visible light image according to the luminance level of the infrared light image is adopted as the chrominance information of the pixel value of the region of the cornea range.

In addition, the chrominance information of the corresponding pixel of the visible light image may also be used directly as the chrominance information of the pixel value of the region of the cornea range. Alternatively, it is possible to switch between a case of directly using the chrominance information of the corresponding pixel of the visible light image and a case of using the corrected chrominance information obtained by performing the level-correction on the chrominance information of the corresponding pixel of the visible light image according to the luminance level of the infrared light image of the visible light image according to the luminance level and the like of the corresponding pixel of the infrared light image, for example.

Alternatively, the chrominance information of the pixel value of the region of the cornea range may be set to a fixed value such as 0, and the region of the cornea range may be achromatic.

Also, in the operative site image presentation processing described above, the image mixing unit 72 performs the processing of detecting the cornea range of the eye of the visible light image and converting the pixel information of the cornea range of the visible light image with the pixel information of the corresponding pixel of the infrared light image as the mixture processing. However, the image mixing unit 72 may also perform processing of replacing a range of the pupil 92 of the visible light image by using the pixel information of the corresponding pixel of the infrared light image. It is also possible to perform processing of replacing an entire image of the visible light image by using the pixel information of the corresponding pixel of the infrared light image. That is, a region subjected to the processing of replacing the visible light image with the pixel value using the pixel information of the infrared light image is not limited to the cornea range of the eye and may be arbitrarily determined.

<Example of Generating Only Infrared Light Image>

The image processing unit 32 may execute a mode in which the above-described processing of replacing the pixel information of the cornea range of the eye of the visible light image with the pixel information of the infrared light image as a first operation mode, execute a mode in which only the infrared light image is generated using the sensor signal supplied from the image sensor 42 to be supplied to the presentation unit 33 to be displayed as a second operation mode, and switch between the first operation mode and the second operation mode as necessary to operate.

Figure 15:
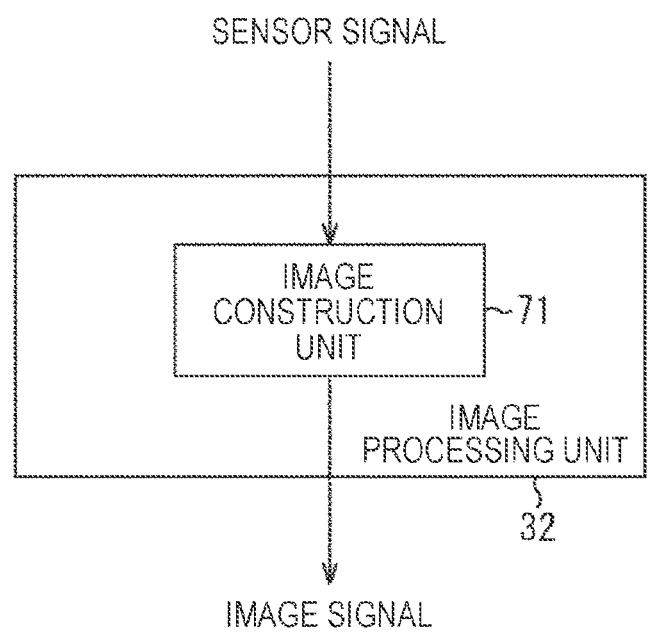
FIG. 15 is a block diagram illustrating a configuration example of the image processing unit.

Alternatively, in a case where the visible light image is not necessary, the image processing unit 32 may also be configured to generate only the infrared light image by using the sensor signal supplied from the image sensor 42. In this case, the image sensor 42 may be the image sensor having the pixel array in which four pixels of the R, G, B, and IR pixels are repeatedly arranged illustrated in FIG. 4, or the image sensor having only the IR pixels illustrated on a right side in FIG. 13. Also, in a case of the configuration of generating only the infrared light image, the image processing unit 32 have a configuration without the image mixing unit 72 as illustrated in FIG. 15.

According to the first embodiment described above, the presentation unit 33 may present the infrared light image or the mixed image using the pixel information of the infrared light image as the stereoscopic image with the high resolution, and the operator may perform an operation while referring to only the image presented by the presentation unit 33.

2. Second Embodiment

<2.1 Configuration Example of Surgical System>

Figure 16:
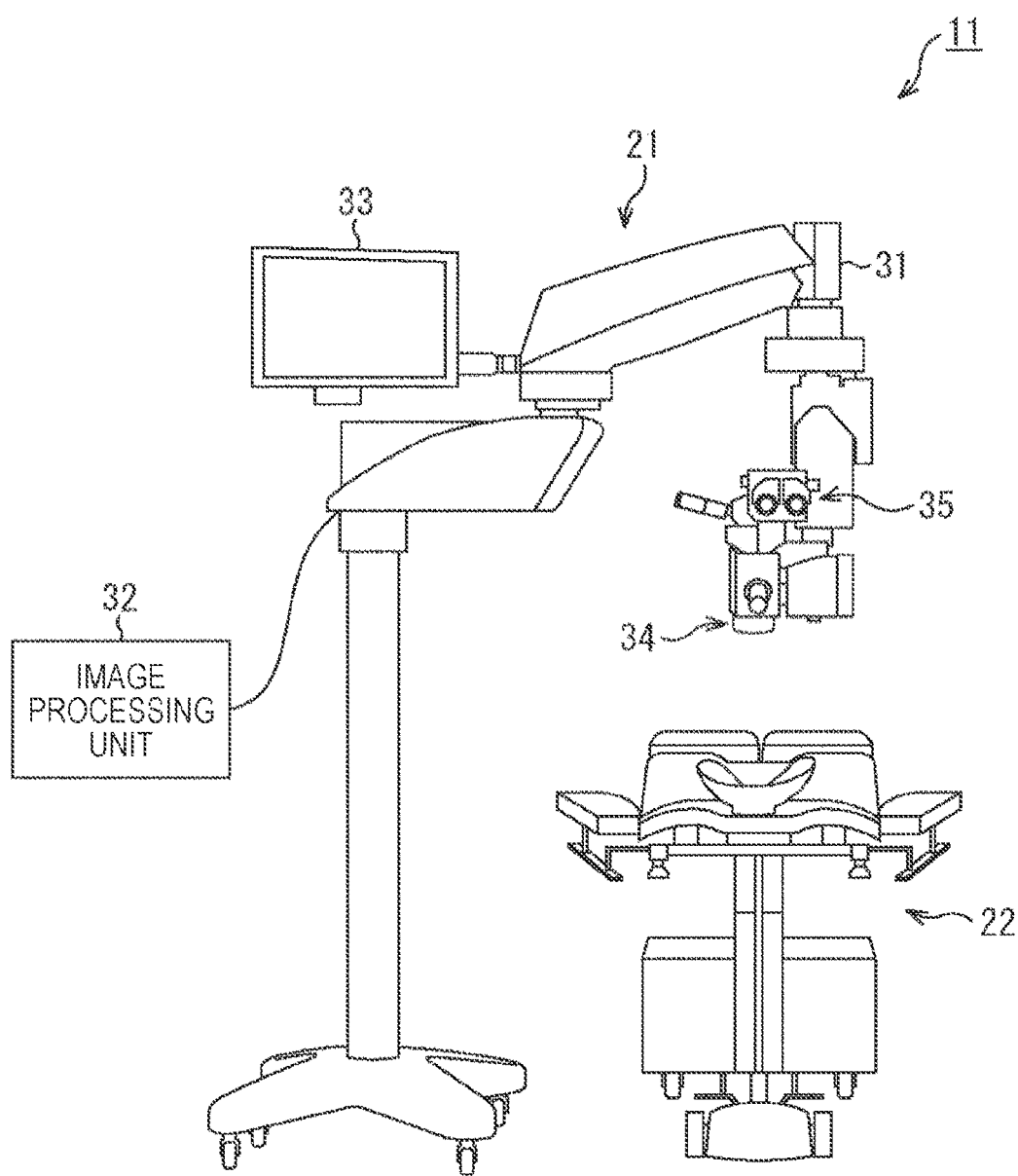
FIG. 16 is a view illustrating a configuration example of a second embodiment of a surgical system to which the present technology is applied.

FIG. 16 is a view illustrating a configuration example of a second embodiment of a surgical system to which the present technology is applied.

In the description of the second embodiment, only a portion different from that of the above-described first embodiment is described.

In a surgical system 11 of the second embodiment, an eyepiece 35 is further provided in a casing 31, and an operator may perform an operation while viewing an image displayed on a presentation unit 33, and also observe the eye of the patient via the eyepiece 35 to perform an operation.

If the presentation unit 33 of the first embodiment is a first presentation unit 33A, a portion presenting an operative site to the operator via the eyepiece 35 in the second embodiment may be a second presentation unit 33B.

<2.2 Configuration Example of Second Presentation Unit>

Figure 17:
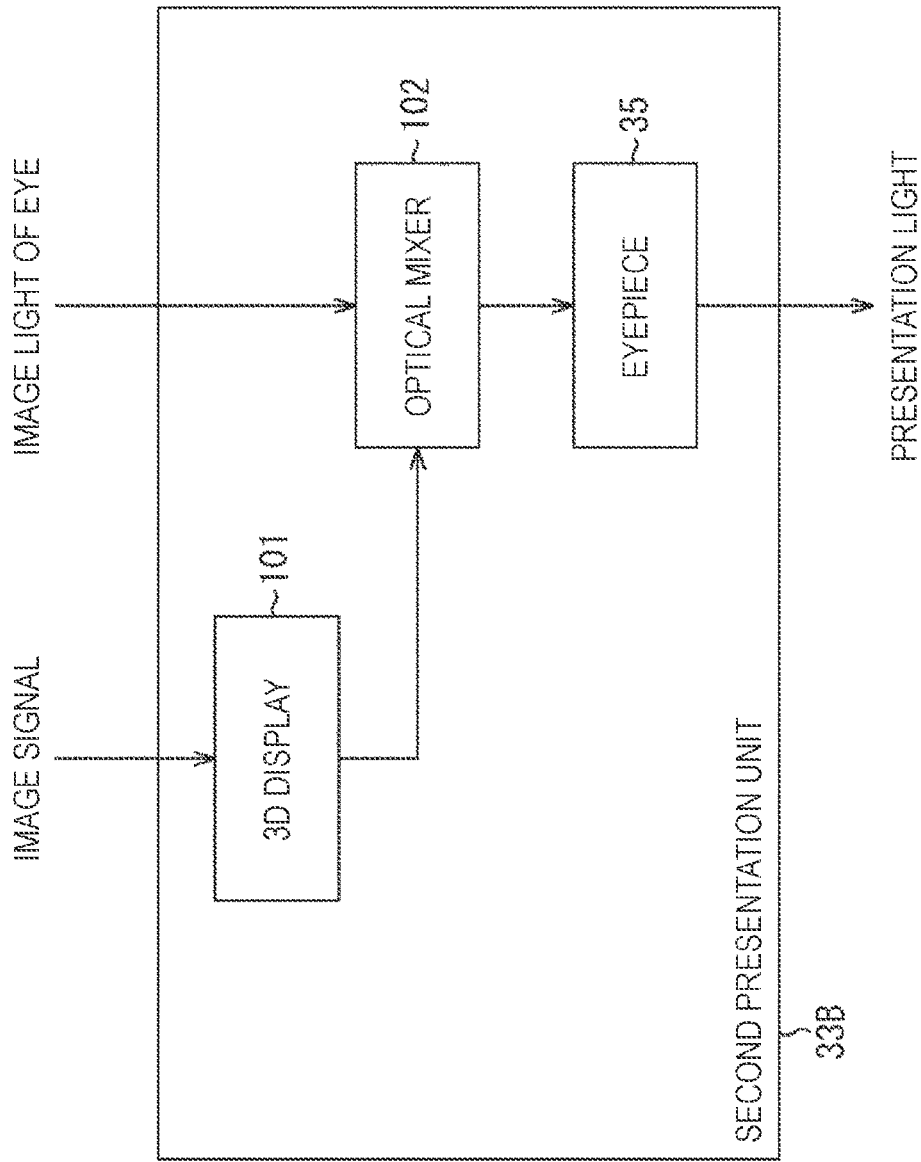
FIG. 17 is a block diagram illustrating a configuration example of a second presentation unit.

As illustrated in FIG. 17, the second presentation unit 33B includes the eyepiece 35, a 3D display 101, and an optical mixer 102.

The 3D display 101 outputs a predetermined image based on an image signal generated by an image processing unit 32 on the basis of sensor signals output from image sensors 42L and 42R to the optical mixer 102. The image output by the 3D display 101 to the optical mixer 102 may be any one of a mixed image, an infrared light image, and a visible light image described in the first embodiment. Also, the image which the 3D display 101 outputs to the optical mixer 102 may be appropriately changed by changing of an operation mode or a setting value.

The optical mixer 102 optically mixes a light flux of a predetermined image output from the 3D display 101 and a light flux of image light of the eye of the patient incident from an imaging optical system 41. An image formed by the light fluxes mixed by the optical mixer 102 is supplied to the eye of the operator via the eyepiece 35.

<2.3 Configuration Example in Casing>

Figure 18:
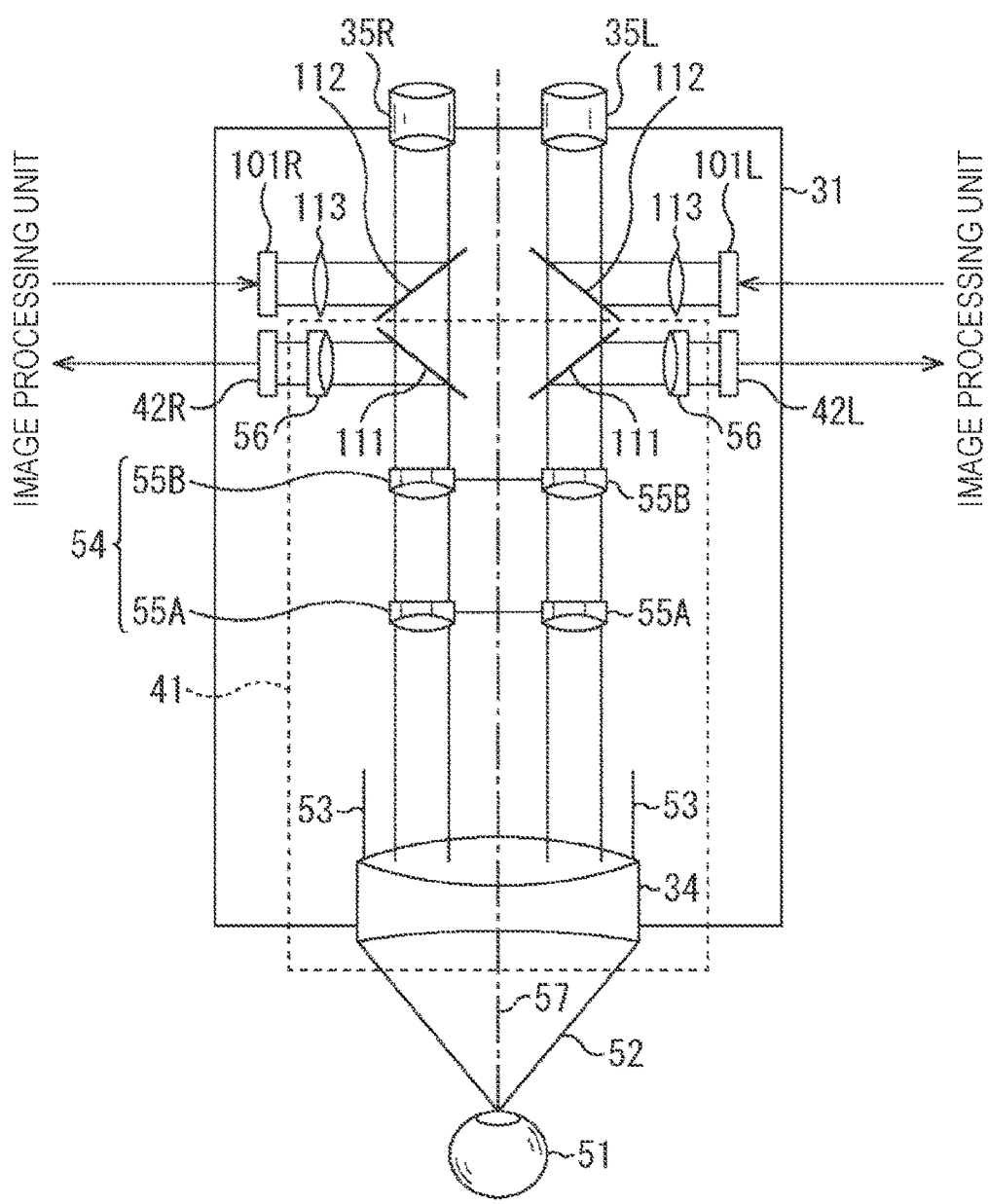
FIG. 18 is a view illustrating a configuration example of an optical system in a casing in a case where the second presentation unit is provided.

FIG. 18 is a view illustrating a configuration example of an optical system in the casing 31 in a case where the second presentation unit 33B is provided.

In FIG. 18, a portion corresponding to that in FIG. 3 in the first embodiment is assigned with the same reference sign and the description thereof is omitted as appropriate.

As illustrated in FIG. 18, the eyepiece 35 includes an eyepiece 35L for the left eye and an eyepiece 35R for the right eye. Similarly, the 3D display 101 also includes a 3D display 101L for the left eye and a 3D display 101R for the right eye.

Two partial light fluxes 58 and 59 corresponding to the left and right eyes pass through two half mirrors 111 and 112 to be incident on the eyepiece 35R and the eyepiece 35L, respectively.

The half mirror 111 distributes the image light of the eye of the patient to the eyepiece 35 and the image sensor 42. The half mirror 112 reflects the light flux of a predetermined image output from the 3D display 101 to be incident via a lens 113 to the eyepiece 35. The half mirror 112 corresponds to the optical mixer 102 in FIG. 17.

The image output from the 3D display 101 to the optical mixer 102 may be any one of the mixed image, the infrared light image, and the visible light image described in the first embodiment, but according to a configuration of the casing 31 illustrated in FIG. 18, the image light of the eye by the visible light may be directly viewed via the imaging optical system 41. Therefore, if the image output from the 3D display 101 is the image different from the visible light image such as the infrared light image, it is possible to present more information regarding the operative site to the operator.

<2.4 Other Configuration Example of Optical Mixer>

Figure 19:
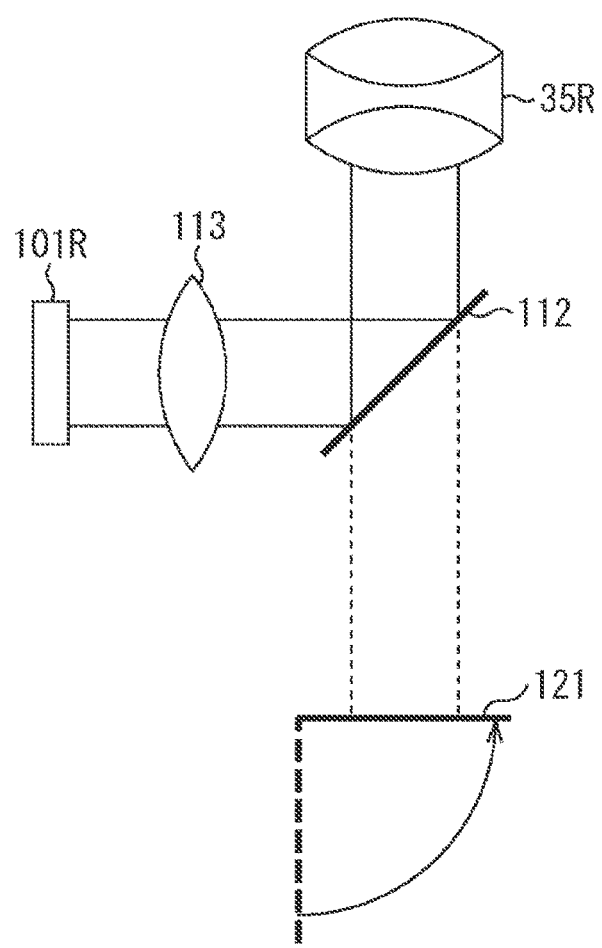
FIG. 19 is a view illustrating another example of an optical mixer 102.

Also, for example, by providing a movable shutter 121 in addition to the half mirror 112 as a part of the optical mixer 102 as illustrated in FIG. 19, it becomes possible to switch between presentation of the image by the mixed light of the image light of the eye via the imaging optical system 41 and the light flux of the infrared light image from the 3D display 101 and presentation of only the infrared light image from the 3D display 101 according to a mode and the like.

Figure 20:
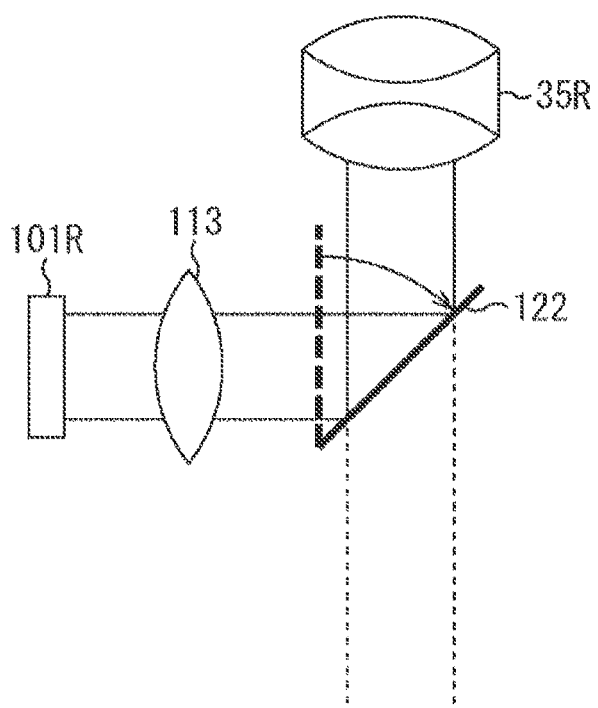
FIG. 20 is a view illustrating still another example of the optical mixer 102.

In a case where it is not necessary to present the image by the mixed light of the image light of the eye via the imaging optical system 41 and the light flux of the infrared light image from the 3D display 101 and it is sufficient to switch between the image light of the eye via the imaging optical system 41 and the infrared light image from the 3D display 101 to present to the operator, a movable mirror 122 may be used in place of the half mirror 112 as illustrated in FIG. 20.

In the above-described second embodiment, the first presentation unit 33A such as the 3D display and the second presentation unit 33B which presents the image by the mixed light of the light flux of a predetermined image output from the 3D display 101 and the image light of the eye of the patient incident from the imaging optical system 41 are provided, but the first presentation unit 33A may also be omitted.

As described above, according to the present technology, the mixed image is generated by using pixel information of the infrared light image to be presented to the operator, so that, for example, a region with low contrast due to opacity of the cornea may be replaced with an image with high contrast to be presented. As a result, the operator may easily observe a site to be operated.

Also, in a case where the mixed image to which color information is added on the basis of chrominance information of the visible light image is generated, in addition to improvement in contrast, the image has a color familiar to the operator, so that this may be more easily viewed.

In the description above, the embodiment in which the present technology is applied to the surgical system 11 used for the eye (ophthalmologic) operation is described, but the present technology may also be applied to a surgical system of not only ophthalmology but also neurosurgery, and to an image processing system which performs diagnosis and the like.

<3. Configuration Example of Computer>

The above-described series of processes may be executed by hardware or may be executed by software. In a case where a series of processes is executed by the software, a program which forms the software is installed on a computer. Herein, the computer includes a computer built in dedicated hardware, a general-purpose personal computer, for example, capable of executing various functions by various programs installed and the like.

Figure 21:
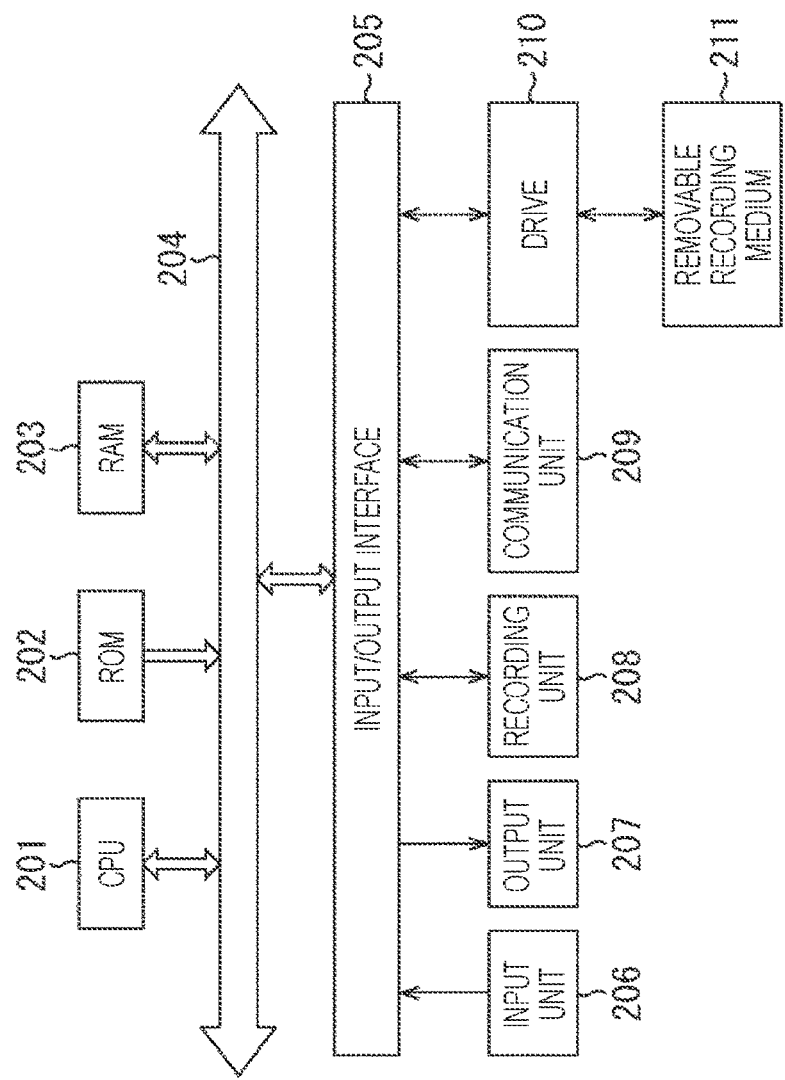
FIG. 21 is a block diagram illustrating a configuration example of one embodiment of a computer to which the present technology is applied.

FIG. 21 is a block diagram illustrating a configuration example of the hardware of the computer which executes the above-described series of processes by the program.

In the computer, a central processing unit (CPU) 201, a read only memory (ROM) 202, and a random-access memory (RAM) 203 are connected to one another via a bus 204.

An input/output interface 205 is further connected to the bus 204. An input unit 206, an output unit 207, a recording unit 208, a communication unit 209, and a drive 210 are connected to the input/output interface 205.

The input unit 206 includes or a keyboard, a mouse, a microphone, an imaging element and the like. The output unit 207 includes a display, a speaker and the like. The recording unit 208 includes a hard disk, a non-volatile memory and the like. The communication unit 209 includes a network interface and the like. The drive 210 drives a removable recording medium 211 such as a magnetic disc, an optical disc, a magnetooptical disc, or a semiconductor memory.

In the computer configured in the above-described manner, the CPU 201 loads the program recorded in the recording unit 208, for example, on the RAM 203 via the input/output interface 205 and the bus 204 to execute, and as a result, the above-described series of processes is performed.

The program executed by the computer (CPU 201) may be recorded in the removable recording medium 211 as a package medium and the like to be provided, for example. Also, the program may be provided by means of a wired or wireless transmission medium such as a local region network, the Internet, and digital broadcasting.

In the computer, the program may be installed on the recording unit 208 via the input/output interface 205 by mounting the removable recording medium 211 on the drive 210. Also, the program may be received by the communication unit 209 via the wired or wireless transmission medium to be installed on the recording unit 208. In addition, the program may be installed in advance on the ROM 202 and the recording unit 208.

Meanwhile, the program executed by the computer may be the program processes of which are performed in chronological order in the order described in this specification or may be the program the processes of which are performed in parallel or at required timing such as when a call is issued.

In this specification, a system is intended to mean assembly of a plurality of components (devices, modules (parts) and the like) and it does not matter whether all the components are in the same casing. Therefore, a plurality of devices stored in different casings connected via the network and one device obtained by storing a plurality of modules in one casing are the systems.

The embodiments of the present technology are not limited to the above-described embodiments and various modifications may be made without departing from the scope of the present technology.

For example, it is possible to adopt a combination of all or some of a plurality of embodiments described above.

For example, the present technology may be configured as cloud computing in which a function is shared by a plurality of devices via the network to process together.

Also, each step described in the above-described flowchart may be executed by one device or executed by a plurality of devices in a shared manner.

Furthermore, in a case where a plurality of processes is included in one step, a plurality of processes included in one step may be executed by one device or by a plurality of devices in a shared manner.

Meanwhile, the effects described in this specification are illustrative only and are not limited; the effects other than those described in this specification may also be included.

Meanwhile, the present technology may also have following configurations.

(1)

A surgical microscope provided with:
- a light receiving unit including at least a pixel having sensitivity to an infrared region;
- an imaging optical system which guides image light of an eye which is light reflected from the eye as an operation target to the light receiving unit; and
- a presentation unit which presents an image based on a sensor signal generated by the light receiving unit.

(2)

The surgical microscope according to (1) described above,
- in which the light receiving unit includes an imaging element including only a pixel having sensitivity to the infrared region.

(3)

The surgical microscope according to (1) described above,
- in which the light receiving unit includes an imaging element including a pixel having sensitivity to the infrared region and a pixel having sensitivity to an R, G, or B region.

(4)

The surgical microscope according to (1) described above,
- in which the light receiving unit includes an imaging element including a pixel having sensitivity to the infrared region and an R region, a pixel having sensitivity to the infrared region and a G region, or a pixel having sensitivity to the infrared region and a B region.

(5)

The surgical microscope according to (1) described above,
in which the light receiving unit includes an imaging element including only a pixel having sensitivity to the infrared region and an imaging element including a pixel having sensitivity to an R, G, or B region.

(6)

The surgical microscope according to any one of (1) to (5) described above,
in which the presentation unit includes a display which displays a stereoscopically viewable image having 3840 or more pixels in a horizontal direction.

(7)

The surgical microscope according to any one of (1) to (6) described above, further provided with:
an image mixing unit which performs mixture processing of images based on a sensor signal generated by the light receiving unit,
in which the light receiving unit includes a pixel having sensitivity to the infrared region and a pixel having sensitivity to a visible light region and generates a first sensor signal obtained from the pixel having sensitivity to the infrared region and a second sensor signal obtained from the pixel having sensitivity to the visible light region, and
the image mixing unit performs the mixture processing on an infrared light image generated by the first sensor signal and a visible light image generated by the second sensor signal to generate a mixed image.

(8)

The surgical microscope according to (7) described above,
in which the image mixing unit generates the mixed image in which a partial region of the visible light image is replaced with a pixel value using pixel information of the infrared light image.

(9)

The surgical microscope according to (8) described above,
in which the pixel information of the infrared light image includes luminance information of the infrared light image.

(10)

The surgical microscope according to (8) described above,
in which the pixel value using the pixel information of the infrared light image is the pixel value using luminance information of the infrared light image and chrominance information of the visible light image.

The surgical microscope according to (10) described above,
in which the pixel value using the pixel information of the infrared light image is the pixel value using the luminance information of the infrared light image and chrominance information obtained by performing level-correction according to a luminance level of the infrared light image on the chrominance information of the visible light image.

(12)

The surgical microscope according to any one of (8) to (11) described above,
in which a partial region of the visible light image is a region of a cornea range of the eye.

(13)

The surgical microscope according to any one of (8) to (11) described above,
in which a partial region of the visible light image is a region of a pupil range of the eye.

(14)

The surgical microscope according to (7) described above,
in which the image mixing unit generates the mixed image in which an entire region of the visible light image is replaced with a pixel value using pixel information of the infrared light image.

(15)

The surgical microscope according to any one of (1) to (14) described above, further provided with:
an optical mixer which mixes a light flux of the image based on the sensor signal generated by the light receiving unit and a light flux of the image light of the eye,
in which the presentation unit presents an image of light fluxes mixed by the optical mixer.

(16)

An image processing device provided with:
an image mixing unit which obtains an infrared light image obtained by imaging an eye as an operation target with an imaging unit having sensitivity to an infrared region and a visible light image obtained by imaging the eye with an imaging unit having sensitivity to a visible light region, and performs mixture processing on the infrared light image and the visible light image to generate a mixed image.

(17)

An image processing method provided with:
a step of obtaining an infrared light image obtained by imaging an eye as an operation target with an imaging unit having sensitivity to an infrared region and a visible light image obtained by imaging the eye with an imaging unit having sensitivity to a visible light region, and performing mixture processing on the infrared light image and the visible light image to generate a mixed image.

REFERENCE SIGNS LIST

11 Surgical system
21 Surgical microscope
31 Casing
32 Image processing unit
33(33A, 33B) Presentation unit
34 Objective lens
35 Eyepiece
41 Imaging optical system
42 Image sensor
51 Eye
71 Image construction unit
72 Image mixing unit
91 Cornea
92 Pupil
101 3D display
102 Optical mixer
111, 112 Half mirror
201 CPU
202 ROM
203 RAM
206 Input unit
207 Output unit
208 Recording unit
209 Communication unit
210 Drive

The invention claimed is:

1. A surgical microscope, comprising:
a light receiving unit including at least a first pixel having sensitivity to an infrared region;
an imaging optical system configured to guide image light of an eye to the light receiving unit, wherein
the image light is reflected from the eye,
the eye is an operation target, and
the light receiving unit is configured to convert the image light of the eye to a sensor signal;
an optical mixer configured to mix a light flux of a first image and a light flux of the image light of the eye, wherein the first image is output based on the sensor signal; and
a presentation unit configured to present a second image based on the light flux of the first image and the light flux of the image light mixed by the optical mixer.

2. The surgical microscope according to claim 1,
wherein the light receiving unit further includes an imaging element including only the first pixel having sensitivity to the infrared region.

3. The surgical microscope according to claim 1,
wherein the light receiving unit further includes an imaging element including the first pixel having sensitivity to the infrared region and a second pixel having sensitivity to one of a red region, a green region, or a blue region.

4. The surgical microscope according to claim 1,
wherein the light receiving unit further includes an imaging element including one of a second pixel having sensitivity to the infrared region and a red region, a third pixel having sensitivity to the infrared region and a green region, or a fourth pixel having sensitivity to the infrared region and a blue region.

5. The surgical microscope according to claim 1,
wherein the light receiving unit further includes a first imaging element including only the first pixel having sensitivity to the infrared region and a second imaging element including a second pixel having sensitivity to one of a red region, a green region, or a blue region.

6. The surgical microscope according to claim 1,
wherein the presentation unit includes a display device configured to display a stereoscopically viewable image having at least 3840 pixels in a horizontal direction.

7. The surgical microscope according to claim 1, further comprising:
an image mixing unit, wherein
the light receiving unit further includes the first pixel having sensitivity to the infrared region and a second pixel having sensitivity to a visible light region,
the light receiving unit is further configured to generate a first sensor signal obtained from the first pixel and a second sensor signal obtained from the second pixel, and
the image mixing unit is configured to execute a mixture process on an infrared light image generated by the first sensor signal and a visible light image generated by the second sensor signal, to generate a mixed image.

8. The surgical microscope according to claim 7,
wherein the image mixing unit is further configured to generate the mixed image in which a partial region of the visible light image is replaced with a first pixel value corresponding to pixel information of the infrared light image.

9. The surgical microscope according to claim 8,
wherein the pixel information of the infrared light image includes luminance information of the infrared light image.

10. The surgical microscope according to claim 8,
wherein the first pixel value corresponding to the pixel information of the infrared light image is equal to a second pixel value corresponding to luminance information of the infrared light image and chrominance information of the visible light image.

11. The surgical microscope according to claim 10,
wherein the second pixel value is obtained based on execution of a level-correction process, according to a luminance level of the infrared light image, on the chrominance information of the visible light image.

12. The surgical microscope according to claim 8,
wherein the partial region of the visible light image is a region of a cornea range of the eye.

13. The surgical microscope according to claim 8,
wherein the partial region of the visible light image is a region of a pupil range of the eye.

14. The surgical microscope according to claim 7,
wherein the image mixing unit is further configured to generate the mixed image in which an entire region of the visible light image is replaced with a pixel value corresponding to pixel information of the infrared light image.

15. An image processing device, comprising:
an image mixing unit configured to:
receive an infrared light image, including an eye as an operation target, from a first imaging unit, wherein
the first imaging unit is sensitive to an infrared region,
the first imaging unit obtains the infrared light image based on image light of the eye, and
the image light is reflected from the eye;
receive a visible light image, including the eye as the operation target, from a second imaging unit, wherein
the second imaging unit is sensitive to a visible light region, and
the second imaging unit obtains the visible light image based on the image light of the eye;
execute a mixture process on the infrared light image and the visible light image;
generate a mixed image based on the execution of the mixture process; and
output the mixed image to an optical mixer, wherein the optical mixer mixes a light flux of the mixed image and a light flux of the image light of the eye to generate an output image.

16. An image processing method, comprising:
receiving, by a first imaging unit, an infrared light image including an eye as an operation target, wherein
the first imaging unit is sensitive to an infrared region,
the first imaging unit obtains the infrared light image based on image light of the eye, and
the image light is reflected from the eye;
receiving, by a second imaging unit, a visible light image including the eye as the operation target, wherein
the second imaging unit is sensitive to a visible light region, and
the second imaging unit obtains the visible light image based on the image light of the eye;
executing a mixture process on the infrared light image and the visible light image;
generating a mixed image based on the execution of the mixture process; and outputting the mixed image to an optical mixer, wherein the optical mixer mixes a light flux of the mixed image and a light flux of the image light of the eye to generate an output image.

* * * * *